(12) United States Patent  (10) Patent No.: US 7,113,832 B2
Longo  (45) Date of Patent: Sep. 26, 2006

(54) INTERSTITIAL MICROWAVE ANTENNA WITH MINIATURIZED CHOKE HYPERTHERMIA IN MEDICINE AND SURGERY

(75) Inventor: Iginio Longo, Pisa (IT)

(73) Assignee: CNR Consiglio Nazionale deile Ricerche, Rome (IT)

( * ) Notice: Subject to any disclaimer, the term of this patent is extended or adjusted under 35 U.S.C. 154(b) by 0 days.

(21) Appl. No.: 10/470,231

(22) PCT Filed: Jan. 31, 2002

(86) PCT No.: PCT/IB02/00299

§ 371 (c)(1), (2), (4) Date: Jul. 25, 2003

(87) PCT Pub. No.: WO02/061880

PCT Pub. Date: Aug. 8, 2002

(65) Prior Publication Data

US 2004/0049254 A1     Mar. 11, 2004

(30) Foreign Application Priority Data

Jan. 31, 2001     (IT) .............................. PI2001A0006

(51) Int. Cl.
*A61F 7/00*     (2006.01)
(52) U.S. Cl. ................... 607/101; 607/102; 607/113; 607/115; 607/156
(58) Field of Classification Search ............ 607/101, 607/102, 113, 115, 116, 154, 155, 156
See application file for complete search history.

(56) References Cited

U.S. PATENT DOCUMENTS 4,448,198 A     5/1984  Turner .................. 128/422

(Continued)

FOREIGN PATENT DOCUMENTS

EP     1055400 A1     11/2000

OTHER PUBLICATIONS

James C. Lin and Yu-Jin Wang, "The Cap-Choke Catheter Antenna for Microwave Ablation Treatment" published in IEEE Transaction on Biomedical Engineering, IEEE Inc. New York, US, vol. 43 No. 6, Jun. 1, 1996.

(Continued)

*Primary Examiner*—Rosiland Rollins
(74) *Attorney, Agent, or Firm*—The Bilicki Law Firm, PC

(57)     ABSTRACT

The present invention relates to minimally invasive surgery techniques. It provides a method for manufacturing an antenna for percutaneous acute hyperthermia microwave applications of the monopole or dipole co-axial type provided with trap, commonly called choke, for blocking the propagation of the backwards reflecting wave towards the generator. The miniaturization of the device allows a use minimally invasive for interstitial hyperthermia in medicine and surgery, in particular for oncology. The method of manufacturing the antenna provides a metal needle (1) for the introduction of the antenna (2,3,4) in the target tissue. On the external conductor (4) of the antenna (2) a metal collar 6 is connected in a predetermined position; a plastics sheath (5) is applied in order to cover the external conductor (2) in the portion between the feed (7) and the collar 6; the inner wall of the metal needle 1 wherein the antenna is inserted is then used for containing and guiding the collar 6 and the sheath 5; in particular, the collar 6 being in electrical contact with the inner wall of the metal needle 1. An antenna is thus obtained with choke of variable length and with miniaturized diameter. A thermocouple can be introduced through the choke that protrudes the directly in the "feed" zone.

14 Claims, 3 Drawing Sheets

U.S. PATENT DOCUMENTS 5,057,106 A * 10/1991 Kasevich et al. .............. 606/33
5,370,676 A * 12/1994 Sozanski et al. ............ 607/101

OTHER PUBLICATIONS

Gerd Schaller, Jurgen Erb, and Rainer Engelbrecht, "Field Simulation of Dipole Antennas for Interstitial Microwave Hyperthermia" published in IEEE Transactions on Microwave Theory and Techniques, IEEE Inc., New York, US, vol. 44, No. 6, Jun. 1, 1996.

Sylvain Labonte, Angeline Blais, Stephane R. Legault, Hassan O. Ali, and Langis Roy, "Monopole Antennas for Microwave Catheter Ablation" published in IEEE Transactions on Microwave Theory and Techniques, IEEE Inc., New York, US, vol. 44, No. 10, part 2, Oct. 1, 1996.

* cited by examiner

INTERSTITIAL MICROWAVE ANTENNA WITH MINIATURIZED CHOKE HYPERTHERMIA IN MEDICINE AND SURGERY

FIELD OF THE INVENTION

The present invention relates to minimally invasive surgery techniques, for interstitial, percutaneous, laparoscopic, endoscopic and intrasurgery applications in medicine and surgery, especially in oncology.

More precisely, it relates to a microwave antenna, for hyperthermia, operating from 37 C up to over 100 C, of the monopole or dipole co-axial type equipped with "trap", commonly called choke, for blocking the propagation of the reflecting wave that turns back towards the generator.

Furthermore the invention relates to a method of construction of such an antenna.

DESCRIPTION OF THE PRIOR ART

Hyperthermia in oncology is method used for over 30 years for treatment of cancer (Hahn GM, Hyperthermia and Cancer, Plenum Press, in the York, 1982). It consists in heating the cancer cells to obtain their necrosis directly or with additional use of other methods such as radiotherapy, chemotherapy or other surgery techniques.

For heating tissues, in particular for treatment of surface lesions, firstly electromagnetic waves have been used produced by a source located out of the human body.

More recently thin appliances have been used among which microwave antennas, operating between some hundreds of MHz and some thousands of MHz, typically at 2450 MHz, executed in co-axial tube, for interstitial, percutaneous, laparoscopic, endoscopic and intrasurgery applications, suitable to the local treatment of deep lesions (Iskander MF & Tumeh AM, Design Optimization of Interstitial Antennas, IEEE Transactions on Biomedical Engineering, 1989, 238–246).

Such antennas are usually inserted in the lesion to treat using catheters or metal needles, under echographic guide, TAC, NMR or other computerised imaging techniques. They are suitable to be used in association with drugs, ionizing waves and/or with surgery ablation.

These microwave antennas, normally, are manufactured using a flexible or semi-rigid co-axial tube, suitably modified at one end, for conveying microwave power into the tissues to cause hyperthermia.

In FIG. 1 an axial cross section is shown of an antenna inserted in a biopsy needle 1. The antenna, in its active portion at the right of the drawing, is suitably configured as radiating dipole or monopole. More precisely, 2 is the external conductor of the co-axial tube, 3 is the dielectric layer that insulates the external conductor from the central conductor 4. The point indicated with 7 is the feeding point, i.e. the active portion of the antenna, commonly called "feed", where the emitted power, normally, is maximum.

The isothermal surfaces that can be obtained by heating a biological tissue (not crossed by large blood vessels) with a normal antenna, that for example is made by cutting at an end a portion of the external conductor 2 of the co-axial tube and leaving dielectric layer 3 uncovered, as described in FIG. 1, have a rotationally symmetric configuration. Their projection on the plane of the figure is elliptical, with a central maximum of transmission, as above said, near feeding point 7 of the antenna, where the distal portion of the external conductor 2 of the co-axial tube is cut. The surface of dotted projection 8 indicates an isothermal surface of the tissue that is being radiated by this type of antenna in a purely theoretical case.

Actually, the impedance of the antenna is never perfectly adapted with that of the medium in which it operates, owing to the variation of the dielectric characteristics of the medium same when heating, and for other reasons connected with the guided propagation of an electromagnetic wave. During the delivery of microwave power there is always an backward wave that returns along the external conductor of the antenna, from the active end towards the generator, causing an backward elongation of the heating figure. The dashed curve 9 indicates the projection of an backwardly elongated isothermal surface corresponding to this effect. This drawback prevents from suitably concentrating the heat production near the active portion of the antenna and is a big limit to the use of this technique.

Per overcome this drawback normally the antenna is equipped with a device, called choke, or trap, often used in radio-broadcasting antennas (see for example Reintjes JF & Coate GT, Principles of Radar, McGraw-Hill Book Company, in the York 1952, p 851) that blocks the backwards propagation of the reflected power.

This device, indicated with 11 in FIG. 2, consists in a co-axial guiding portion, $\lambda/4$ long, being $\lambda$ the wavelength of the emitted waves, obtained by arranging at an end the external conductor of the co-axial tube of the antenna, near the feed 7, a short circuit metal tube 12. In FIG. 2, 1 is the needle guide of the antenna, 2 is the external conductor of the antenna, 3 is the insulating material and 4 is the central conductor.

In this case the backwards reflecting wave, indicated with 13, runs the external surface of the antenna, enters choke 11, reflects itself at its end in a short circuit and, after a total path of $\lambda/2$ is again at the entrance of the choke but in phase opposition with respect to that that at inlet, with a result of a null intensity. The isothermal surface that is obtained when the antenna is equipped with choke 11 is indicated by the continuous curve 10 of FIG. 2.

Actually, as it can be seen, the introduction of the choke 11 causes a substantial increase of the diameter of the antenna, and then of needle 1, thus limiting its applications when a minimum invasive operation is required, such as for example in out-patient's departments, in the repeated treatments, etc.

For manufacturing reasons, and because of the resistance limits of the material, the radial dimension of the choke cannot be reduced under certain limits.

Furthermore, in case of change of the dielectric characteristics of the medium caused by the variation of the temperature during the treatment, or in case of variation of the frequency of the antenna, as when a microwave generator with adjustable frequency, the choke cannot be lengthened or shortened, in order to be always about a fourth of the wavelength long. The impedance of the existing chokes is therefore fixed, whereby the elimination of the returning wave can not be totally effective when the operating temperature is changed.

An application of hyperthermia is, furthermore normally associated to a measure of the local temperature. In fact, it is necessary for measure the heating temperature of the cancer lesions, or other lesions to treat, to preserve the adjacent healthy tissues and for controlling the actual heating power of the antenna.

Usually, in the operation region a sensor of temperature is inserted (indicated with 20 in FIG. 2) For example, metal thermocouples are used. However, they cannot be introduced during the delivery of energy by the antenna, owing to eddy currents in the metal of thermocouple, that overheats thus affecting the measure. Furthermore the presence of a thermocouple changes the distribution of the microwave field, changing the heating pattern. Therefore, the temperature measure with a metal thermocouple must be done with the drawback of stopping often the delivery of energy. Alternatively, optical-fibre sensors are known to have no metal and are not affected by the field or do not perturbate it, but have the drawback of being expensive and fragile. In both cases of metal thermocouples or optical-fibre sensors, there is the further drawback of introducing a further catheter for guiding the sensor into the operation region.

SUMMARY OF THE INVENTION

It is object of the present invention to provide an co-axial microwave antenna for applications in medicine and surgery that is provided with trap, or choke, for blocking the backwards propagation of the reflecting wave towards the generator, wherein a miniaturisation of this trap with respect to the prior art is possible, in order to allow the use for minimally invasive applications.

It is another object of the present invention to provide an antenna that, in case of variation of the medium wavelength, allows the choke to be lengthened or shortened for a more correct operation.

It is a further object of the present invention to provide an antenna that allows a measure of temperature operation region.

It is a further object of the present invention to provide a method for the production of a such an antenna that allows this miniaturisation with simple construction.

These and other objects are achieved by the antenna according to the present invention, that can be inserted in a metal needle necessary for the introduction of the antenna in the target tissue, the antenna having:

an inner conductor, a dielectric layer that coats the inner conductor for all its length, an external conductor that covers coaxially the dielectric layer except from an end portion, a choke mounted outside the external conductor near the end portion, the choke comprising a co-axial conducting portion of diameter higher than the external conductor, a conducting collar for connecting the co-axial conductor to the external conductor, the conducting collar being arranged along the co-axial conducting portion opposite to the end portion, the characteristic of the antenna being that the co-axial conducting portion of the choke consists in the metal needle same.

Advantageously, the collar is in sliding contact with the needle, whereby the length of the choke can be changed.

Preferably, next to the collar and adjacent to the end portion, the antenna has a plastics sheath that is a dielectric layer in the choke.

The sheath can be of antiadhesive material and of length that protrudes from the needle, preventing the outer portion to adhere to tissues during the high temperature heating treatment.

Advantageously, a thermocouple is provided put through the choke and the sheath, said thermocouple being in contact with the external conductor of said co-axial tube and having the sensitive end that comes out from said sheath protruding into the zone of feed of the antenna.

According to another aspect of the invention, a method of construction of a choke with variable length on a co-axial antenna, the antenna being inserted in a metal needle necessary for the introduction of the antenna in the target tissue, the antenna having:

an inner conductor, a dielectric layer that coats the inner conductor for all its length, an external conductor that covers coaxially the dielectric layer except from an end portion, the characteristic being that of providing on the antenna a conducting collar near the end portion, whereby the conducting collar slides in the metal needle.

Preferably, next to the collar adjacent to the end portion a plastics sheath is arranged on the antenna that is a dielectric layer in the choke.

The sheath and the dielectric layer of the antenna are advantageously of PTFE.

The collar can be made of metal welded to the external conductor of the antenna.

According to a further aspect of the invention an antenna for hyperthermia, that can be inserted in a metal needle necessary for the introduction of the antenna in the target tissue, comprises:

an inner conductor, a dielectric layer that coats the inner conductor for all its length, an external conductor that covers coaxially the dielectric layer except from an end portion, a choke mounted outside the external conductor near the end portion, the choke comprising a co-axial conducting portion of diameter higher than the external conductor, the characteristic being of providing a thermocouple put through the choke, said thermocouple being in contact with said external conductor and having the sensitive end that comes out from said choke and protrudes into the zone of feed of the antenna.

BRIEF DESCRIPTION OF THE DRAWINGS

Further characteristics and advantages of the interstitial microwave antenna and of the method for its production, according to the present invention, will be made clearer with the following description of an embodiment thereof, exemplifying but not limitative, with reference to the further attached drawings wherein.

DESCRIPTION OF A PREFERRED EMBODIMENT

Figure 3:
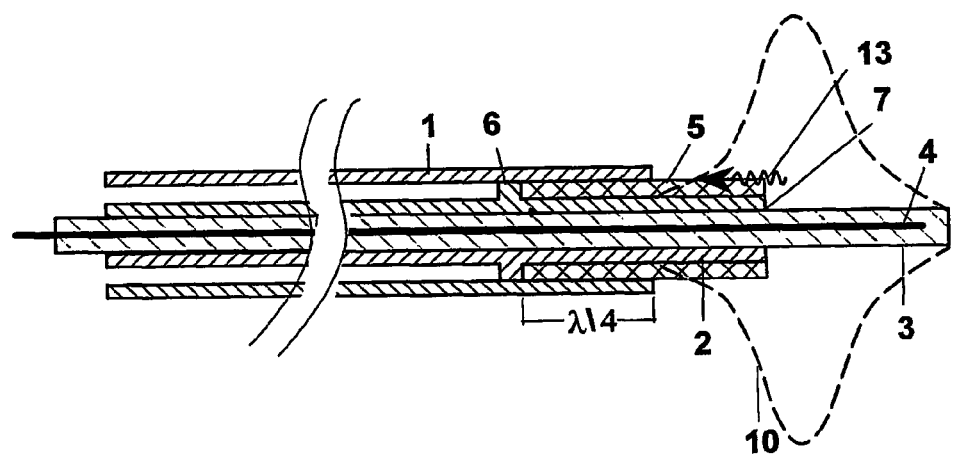
FIG. 3 shows a sectional axial view of an antenna second invention.
Figure 4:
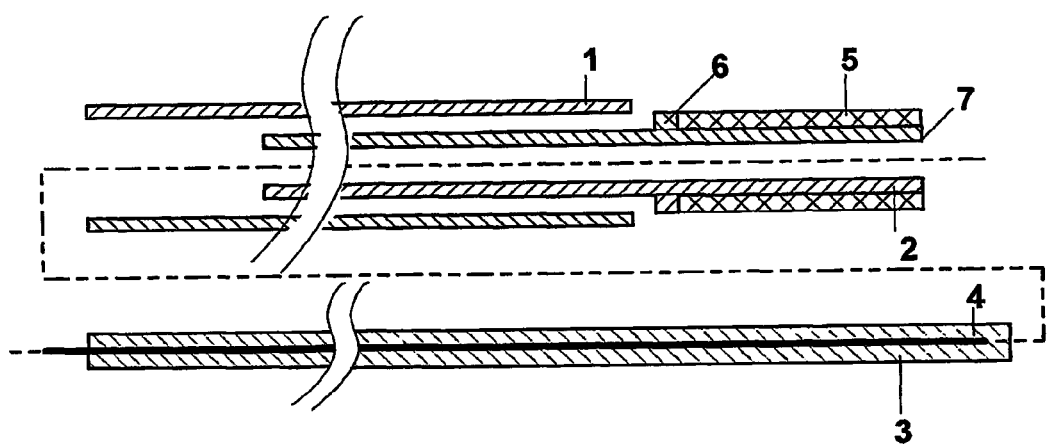
FIG. 4 shows an exploded view of the antenna of FIG. 3.

In FIG. 3 an axial cross section is shown of an antenna according to the invention inserted in a metal tube that consists in an biopsy needle 1, for example a 14 Gauge, outer diameter=mm 2.1 needle.

The antenna, in its active portion at the right of the figure, is a radiating dipole or monopole. More precisely, the antenna is formed by a co-axial tube having an external conductor 2, by a dielectric layer 3 and by a central conductor 4 immersed in the dielectric layer 3 that insulates it from the external conductor 2. The external conductor 2, as well known, has an end point indicated with 7, which is the feeding point, i.e. the active portion of the antenna, normally called "feed", where the emitted power, normally, is maximum.

According to the invention, a plastics insulating sheath 5 and a metal collar 6 are provided. More precisely, this can be obtained:

welding on the external conductor of the antenna 2 the metal collar 6 in a predetermined position, by arranging the sheath 5 of plastics that coats the external conductor 2 in the portion that goes from feed 7 up to collar 6, using the wall inner of the same metal needle 1 wherein the antenna is inserted for containing and guiding the collar 6 and the sheath 5, in particular, the collar 6 being in electrical contact with the wall inner of the metal needle 1.

The invention allows to make in a easy and not expensive way a miniaturized microwave antenna equipped with choke, suitable for local treatment of deep lesions in medicine and surgery. In fact, in combination with the metal needle 1, the collar 6 and the sheath 5 allow to obtain a choke of variable length and made reducing to the minimum the increase of the outer diameter of the antenna.

Figure 2:
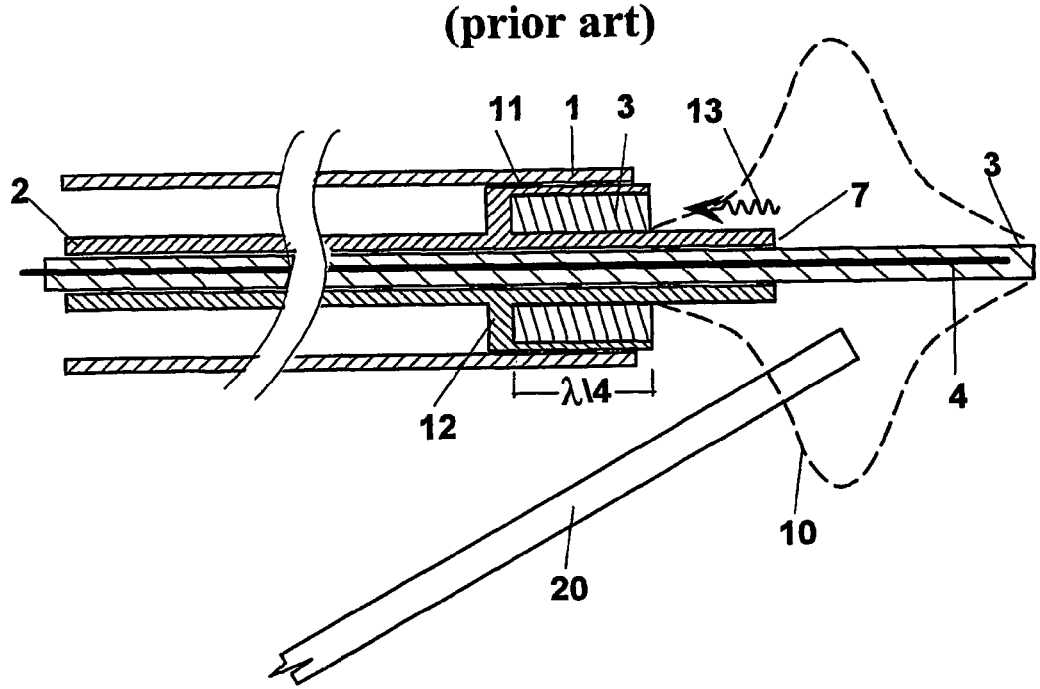
FIG. 2 shows a sectional axial view of an antenna according to the prior art, including the choke.

Like the choke of FIG. 2, in fact, in FIG. 3 the wave 13 is reflected back starting from the feed 7 and runs the external surface of the antenna, enters the choke formed between the needle 1 and the external conductor 4, reflects itself on the collar 6 in short circuit and, after a total $\lambda/2$ path is again at the inlet of the choke in phase opposition with respect to the wave at the inlet, obtaining a null intensity. The variation of wavelength in case of temperature rise, or other cause, can be corrected by varying the position of the collar 6 with respect to needle 1, so that the choke is always $\lambda/4$ long. Within a certain range the variation of impedance of the antenna during the operation can be compensated in the same way changing the length of the choke and then of the portion between the choke and the feed.

Figure 1:
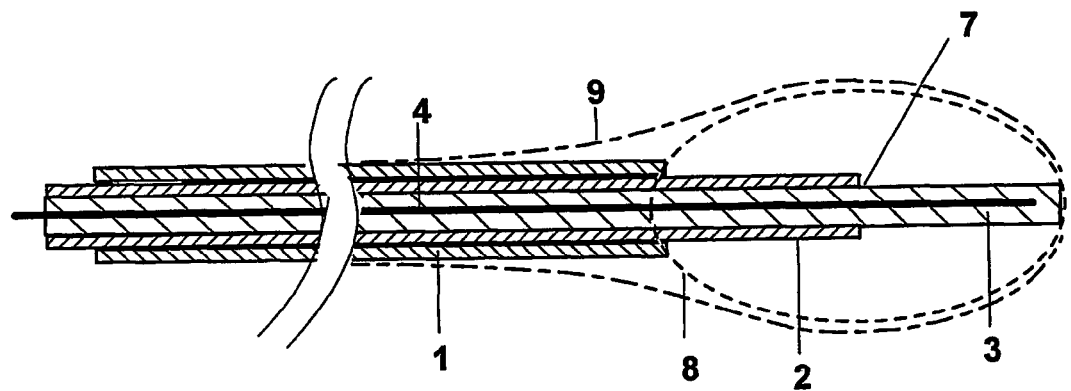
FIG. 1 shows a sectional axial view of an antenna according to the prior art.

The isothermal surface that is obtained when the antenna is equipped with the choke according to the invention is shown also in this case by the dashed curve 10. The heat that is delivered according to this curve allows a local heating in the target tissues without the drawback of the backwards reflecting wave of FIG. 1. This is possible without increasing substantially the diameter, using the sliding contact between the metal collar 6, mounted on the external conductor 2 of the co-axial tube of the antenna, and the inner wall 1 of the needle guide through which the antenna is inserted.

More precisely, the metal collar 6 keeps the electrical contact with the inner wall of the needle guide 1 and is thus a mobile by-pass.

Sheath 5 has, then, the following functions:

is a co-axial wave guide $\lambda/4$ long supplying an effective choke for the antenna, it is a centering element for the sliding in the antenna needle, in the portion outer to the choke the adhesion of tissues is avoided during the high temperature heating treatment, and it does not allow their contact with metal surfaces different from the needle guide within which the antenna slides.

Figure 5:
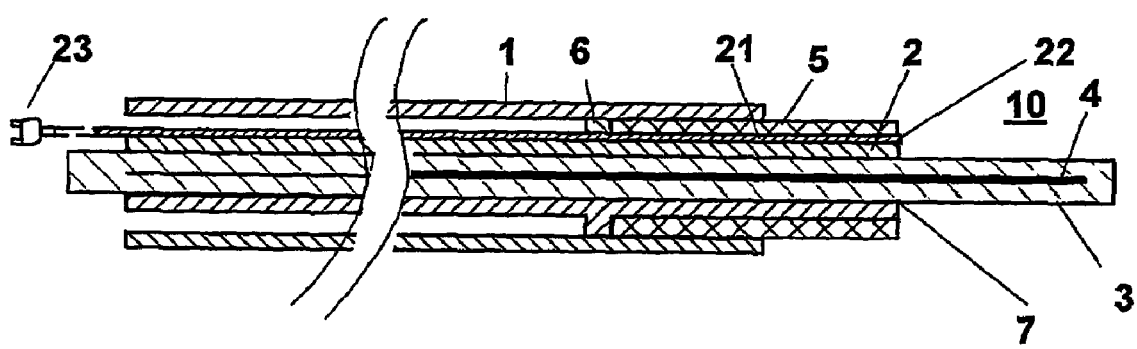
FIG. 5 shows the antenna of FIG. 3 to which a thermocouple is added that crosses the choke and protrudes into the zone of feed.

With reference to FIG. 5, according to a different embodiment of the invention, a thermocouple is provided 21 put through the collar 6 and the sheath 5 that forms the choke. Thermocouple 21 is in contact with the external conductor 2 of the co-axial tube that forms the antenna, and has its sensitive end 22 that comes out from the sheath 5 protruding into the zone 10 of feed of the antenna. The other end of thermocouple is connected to the a temperature measuring instrument not shown by means of a plug 23.

According to the invention thermocouple 21 does not affects the operation of the antenna. In fact, the thermocouple is integral to the metal of the outer co-axial conductor 2. Therefore, thermocouple 22 is practically shielded.

Thermocouple 21 can be a common metal thermocouple, formed by a metal sheath in which are metal different conductors are joined at the sensitive end 22. Such a metal thermocouple not much expensive, much less than in optical fibre sensors (for example fluoride-optical sensors).

A further advantage of thermocouple 21 is that of an external thermocouple has not to be inserted through an additional catheter to part and, especially, the measure can be made directly in the operation region during the feeding delivery that produces the hyperthermia.

Thermocouple 21 can be put also in hyperthermia antennas different from that shown in figures from 3 to 5.

The foregoing description of a specific embodiment will so fully reveal the invention according to the conceptual point of view, so that others, by applying current knowledge, will be able to modify and/or adapt for various applications such an embodiment without further research and without parting from the invention, and it is therefore to be understood that such adaptations and modifications will have to be considered as equivalent to the specific embodiment. The means and the materials to realise the different functions described herein could have a different nature without, for this reason, departing from the field of the invention. It is to be understood that the phraseology or terminology employed herein is for the purpose of description and not of limitation.

What is claimed is:

1. A co-axial microwave antenna for applications selected from a group comprised of interstitial, percutaneous, laparoscopic, endoscopic, and intrasurgery in medicine and surgery, and acute hyperthermia in oncology, wherein said antenna can be inserted into a metal needle for introduction into a target tissue, said antenna comprising:

an inner conductor;

a dielectric layer, wherein said dielectric layer coats said inner conductor substantially along its entire length;

an external conductor that covers coaxially said dielectric layer except for an end portion of said dielectric layer;

a choke mounted outside said external conductor near said end portion, said choke comprising a co-axial conducting portion of a diameter greater than said external conductor; and a conducting collar for connecting said co-axial conducting portion to said external conductor, said conducting collar being arranged along said co-axial conducting portion opposite to said end portion, wherein an inner surface of said needle acts as said co-axial conducting portion of said choke.

2. The antenna according to claim 1, wherein said collar is in sliding contact with said needle, whereby said length of said choke is adjustable.

3. The antenna according to claim 1, wherein a plastic sheath is positioned substantially adjacent to said collar, said plastic sheath acting as a dielectric layer of said choke.

4. The antenna according to claim 3, wherein said sheath is constructed of an anti-adhesive material and has a length that protrudes from said needle, preventing an outer portion of said needle from adhering to said target tissue during a high temperature heating treatment.

5. The antenna according to claim 1, wherein a thermocouple is provided put through the collar and the sheath that forms the choke, said thermocouple being in contact with the external conductor of said co-axial tube and having the sensitive end that comes out from said sheath protruding into the zone of feed of the antenna.

6. A method for using a variable length choke on a co-axial microwave antenna for interstitial, percutaneous, laparoscopic, endoscopic, and intrasurgery applications in medicine and surgery, and for acute hyperthermia in oncology, said method comprising the steps of:
inserting said antenna into a metal needle, said antenna comprised of:
an inner conductor;
a dielectric layer disposed on and substantially encasing said inner conductor;
an external conductor coaxially covering said dielectric layer except for an end portion of said dielectric layer; and
a conducting collar positioned substantially near said end portion of said dielectric layer, whereby said conducting collar slides within said metal needle; and
introducing said needle into a target tissue, said needle functioning as a choke and wherein said needle punctures said target tissue of a patient in a predetermined direction and crosses said tissue to locate an end of said needle in a predetermined point of said tissue.

7. The method according to claim 6, wherein a plastic sheath is provided next to said collar and adjacent to said end portion, wherein said sheath acts as a dielectric layer for said choke.

8. The method according to claim 6, wherein said sheath and the dielectric layer of the antenna are made of a material selected from a group comprised of PTFE.

9. The method according to claim 6, wherein said collar is made of a metal and welded to said external conductor of said antenna.

10. A co-axial microwave antenna for hyperthermia that can be inserted within a metal needle necessary for the introduction of said antenna into a target tissue, said antenna comprising:
an inner conductor;
a dielectric layer, said dielectric layer coating said inner conductor for substantially all its length;
an external conductor that covers coaxially said dielectric layer except for an end portion of said dielectric layer;
a choke mounted outside said external conductor near said end portion of said dielectric layer, said choke comprising a co-axial conducting portion of a diameter greater than a diameter of said external conductor; and
a thermocouple having a sensitive end positioned near a zone of feed of said antenna, said thermocouple being in contact with said external conductor and arranged through the choke with said sensitive end extending out of said choke into a zone of feed of said antenna.

11. The antenna according to claim 10, wherein an inner surface of said needle aids in acting as said choke.

12. The antenna according to claim 10, wherein said device is further comprised of a collar, said collar being in sliding contact With said needle, whereby said choke is adjustable.

13. The antenna according to claim 12, wherein a plastic sheath is positioned substantially adjacent to said collar, wherein an end portion of said sheath is provided that is a second dielectric layer of said choke.

14. The antenna according to claim 13, wherein said sheath is constructed of an anti-adhesive material and protrudes from said needle, preventing an outer portion of said needle from adhering to said target tissue during treatment.

* * * * *